United States Patent [19]
Lee et al.

[11] Patent Number: 5,882,676
[45] Date of Patent: Mar. 16, 1999

[54] SKIN PERMEATION ENHANCER COMPOSITIONS USING ACYL LACTYLATES

[75] Inventors: Eun Soo Lee, Redwood City; Su Il Yum, Los Altos, both of Calif.

[73] Assignee: Alza Corporation, Palo Alto, Calif.

[21] Appl. No.: 452,468

[22] Filed: May 26, 1995

[51] Int. Cl.⁶ .................................................. A61M 37/00
[52] U.S. Cl. ........................ 424/449; 424/448; 514/947
[58] Field of Search .................................. 424/449, 448; 514/946, 947; 604/304, 307

[56] References Cited

U.S. PATENT DOCUMENTS

| | | | |
|---|---|---|---|
| 3,472,931 | 10/1969 | Stoughton | 424/180 |
| 3,527,864 | 9/1970 | MacMillan et al. | 424/177 |
| 3,598,122 | 8/1971 | Zaffaroni | 128/268 |
| 3,598,123 | 8/1971 | Zaffaroni | 128/155 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,130,667 | 12/1978 | Smith | 424/361 |
| 4,144,317 | 3/1979 | Higuchi et al. | 424/21 |
| 4,184,978 | 1/1980 | France et al. | 252/309 |
| 4,286,592 | 9/1981 | Chandrasekaran | 128/260 |
| 4,301,820 | 11/1981 | Cannell et al. | 132/7 |
| 4,314,557 | 2/1982 | Chandrasekaran | 128/260 |
| 4,335,115 | 6/1982 | Thompson et al. | 424/181 |
| 4,379,454 | 4/1983 | Campbell et al. | 604/897 |
| 4,568,343 | 2/1986 | Leeper et al. | 604/896 |
| 4,660,368 | 4/1987 | Allison et al. . | |
| 4,702,916 | 10/1987 | Geria | 424/400 |
| 4,746,515 | 5/1988 | Cheng et al. | 424/449 |
| 4,788,062 | 11/1988 | Gale et al. | 424/449 |
| 4,863,738 | 9/1989 | Taskovich | 424/449 |
| 4,863,970 | 9/1989 | Patel et al. | 514/784 |
| 5,124,354 | 6/1992 | Green | 514/520 |
| 5,314,694 | 5/1994 | Gale et al. | 424/448 |
| 5,344,651 | 9/1994 | Schwen et al. | 424/402 |
| 5,378,730 | 1/1995 | Lee et al. | 514/535 |
| 5,505,956 | 4/1996 | Kim et al. . | |

FOREIGN PATENT DOCUMENTS

| | | | |
|---|---|---|---|
| 0572271 | 12/1993 | European Pat. Off. | A01N 37/36 |
| 0573253 | 12/1993 | European Pat. Off. | A61K 7/06 |
| 1001949 | 7/1962 | Germany | A61K 3/00 |
| WO8806880 | 9/1988 | WIPO | A61K 9/06 |
| WO9505153 | 2/1995 | WIPO | A61K 7/48 |
| WO9509006 | 4/1995 | WIPO | A61K 47/14 |

*Primary Examiner*—Edward J. Webman
*Attorney, Agent, or Firm*—Michael J. Rafa; Paul Sabatine; Steven F. Stone

[57] ABSTRACT

The present invention is directed to the transdermal administration of a drug together with a suitable amount of an acyl lactylate permeation enhancer. The invention includes a transdermal drug delivery device comprising a matrix adapted to be placed in drug- and- permeation enhancer-transmitting relation with a skin site. The matrix contains sufficient amounts of an acyl lactylate permeation enhancer and drug, in combination, to continuously administer drug to the systemic circulation of a patient at a therapeutically effective rate. The invention is also directed to compositions and methods for transdermal administration of a drug together with an acyl lactylate permeation enhancer, alone or in combination with other enhancers.

19 Claims, 5 Drawing Sheets

| FORMULATION 1 | | FORMULATION 4 | |
|---|---|---|---|
| LAUROYL LACTIC ACID | 20% | CAPROYL LACTIC ACID | 20% |
| GML | 20% | L-DEA | 20% |
| EVA40%va | 50% | EVA40%va | 50% |
| TESTOSTERONE | 10% | TESTOSTERONE | 10% |

| FORMULATION 6 | | FORMULATION 8 | |
|---|---|---|---|
| LAURYL LACTATE | 12% | LAURYL LACTATE | 12% |
| LACTIC ACID | 3% | LACTIC ACID | 3% |
| GML | 20% | L-DEA | 20% |
| EVA40%va | 55% | EVA40%va | 55% |
| TESTOSTERONE | 10% | TESTOSTERONE | 10% |

| FORMULATION 10 | | FORMULATION 12 | |
|---|---|---|---|
| LAUROYL LACTIC ACID | 20% | LAUROYL LACTIC | 12% |
| M-DEA | 20% | LACTIC ACID | 3% |
| EVA40%va | 50% | M-DEA | 20% |
| TESTOSTERONE | 10% | EVA40%va | 55% |
| | | TESTOSTERONE | 10% |

CONTROL

| EVA40%va | 98% |
|---|---|
| TESTOSTERONE | 2% |

FIG. 6b

SKIN PERMEATION ENHANCER COMPOSITIONS USING ACYL LACTYLATES

FIELD OF THE INVENTION

This invention relates to the transdermal delivery of drugs or other biologically active agents and more particularly to methods and compositions for enhancing the percutaneous absorption of drugs or other agents when incorporated in transdermal drug delivery systems or devices. Particularly, this invention relates to the use of acyl lactylates as permeation enhancers for transdermal systems or compositions.

DESCRIPTION OF TERMS

As used herein, the term "transdermal" delivery or administration refers to the delivery or administration of agents by permeation through a body surface or membrane, preferably intact skin, by topical administration.

As used herein, the term "therapeutically effective" amount or rate refers to the amount or rate of drug or active agent needed to effect the desired therapeutic result.

As used herein, the phrase "sustained time period" intends at least about 12 hours and will typically intend a period in the range of about one to about seven days.

As used herein, the phrase "predetermined area of skin" intends a defined area of intact unbroken skin or mucosal tissue. That area will usually be in the range of about 5 cm$^2$ to about 100 cm$^2$.

As used herein, the expressions "drug" and "agent" are used interchangeably and are intended to have their broadest interpretation as to any therapeutically active substance which is delivered to a living organism to produce a desired, usually beneficial, effect.

BACKGROUND OF THE INVENTION

Acyl lactylates are represented by the general structure: R—CO—(OCH CH$_3$ CO)$_n$—OH where R is a straight or branched alkyl or aryl group consisting of 3 to 20 carbons and n=1 to 10. Acyl lactylates have been used in the food industry as dough conditioners and softeners and as oil-in-water emulsifiers in nondairy compositions such as coffee whiteners and vegetable oil based whipped toppings. They have also been used as emulsifiers in analgesic stick compositions and in conjunction with other co-emulsifiers to produce an emulsion base for cosmetic or pharmaceutical compositions. Typically, acyl lactylates are commercially available as a salt form for use in cosmetic formulations. The salt form is not effective as a permeation enhancer.

Other uses of acyl lactylates include their use as antimicrobial or antibacterial agents, and as a protectant against hair loss or in topical compositions for inducing, maintaining, or increasing hair growth. In general, permeation enhancers that are not normally toxic at the concentrations employed in cosmetic or medical compositions may exhibit toxic effects at the higher concentrations required to produce adequate permeation enhancement. Accordingly, acyl lactylates have not been used as a permeation enhancer alone or in combination with other permeation enhancing agents in order to increase the permeability of a body surface or membrane to a drug or active agent to transdermally deliver the drug or agent to the systemic circulation of a patient.

U.S. Pat. No. 4,184,978, incorporated herein in its entirety by reference, describes stable oil-in-water emulsion systems for use in cosmetics, toiletries, and pharmaceuticals. Acyl lactylates are disclosed as suitable emulsifiers.

U.S. Pat. No. 4,301,820, incorporated herein in its entirety by reference, describes a composition comprising at least one fatty acid lactylate and/or glycolate as a humectant compound in permanent waving compositions.

U.S. Pat. No. 4,702,916, incorporated herein in its entirety by reference, describes the use of acyl lactylates as emulsifiers in analgesic gel stick compositions.

U.S. Pat. No. 5,124,354, incorporated herein in its entirety by reference, describes a special protein tyrosine kinase inhibitor and a cosmetically acceptable vehicle. Surface active agents, including acyl lactylates, are disclosed as penetration enhancers that improve delivery of the composition to its site of action in the immediate environment of the hair follicle close to the dermal papilla.

European Patent Application 0 573 253 incorporated herein in its entirety by reference describes an anti-bacterial cosmetic composition for topical application to the skin and/or hair comprising $C_6$–$C_{12}$ acyl lactylate or a derivative thereof as an anti-bacterial substance. The composition is especially beneficial in the treatment of unwanted hair loss.

European Patent Application 0 572 271 incorporated herein in its entirety by reference describes the use of acyl lactylates as preservatives in topical cosmetic compositions for prevention of the growth of undesired microorganisms in the skin or hair.

The transdermal route of parenteral delivery of drugs provides many advantages, and transdermal systems for delivering a wide variety of drugs or other beneficial agents are described in U.S. Pat. Nos. 3,598,122; 3,598,123; 3,731,683; 3,797,494; 4,286,592; 4,314,557; 4,379,454; 4,435,180; 4,559,222; 4,568,343; 4,573,999; 4,588,580; 4,645,502; 4,704,282; 4,816,258; 4,849,226; 4,908,027; 4,943,435; and 5,004,610, for example, all of which are incorporated herein by reference. In many cases, drugs which would appear to be ideal candidates for transdermal delivery are found to have such low permeability through intact skin that they cannot be delivered in therapeutically effective amounts from reasonably sized devices.

In an effort to increase skin permeability so that drugs can be delivered in therapeutically effective amounts, it has been proposed to pretreat the skin with various chemicals or to concurrently deliver the drug in the presence of a permeation enhancer. Various materials have been suggested for this, as described in U.S. Pat. Nos. 3,472,931; 3,527,864; 3,896,238; 3,903,256; 3,952,099; 4,046,886; 4,130,643; 4,130,667; 4,299,826; 4,335,115; 4,343,798; 4,379,454; 4,405,616; 4,746,515; 4,788,062; 4,820,720; 4,863,738; 4,863,970; and 5,378,730; British Pat. No. 1,011,949; and Idson, "Percutaneous Absorption," *J. Pharm. Sci.* (1975) 64:901–924.

To be considered useful, a permeation enhancer should have the ability to enhance the permeability of the skin for at least one and preferably a significant number of drugs. More importantly, it should be able to enhance the skin permeability such that the drug delivery rate from a reasonably sized system (preferably 5–50 cm$^2$) is at therapeutically effective levels. Additionally, the enhancer when applied to the skin surface, should be non-toxic, non-irritating on prolonged exposure and under occlusion, and non-sensitizing on repeated exposure. Preferably, it should be odorless and capable of delivering drugs without producing burning or tingling sensations.

SUMMARY OF THE INVENTION

According to the present invention, it has been discovered that acyl lactylates are effective in enhancing the permeation of drugs through body surfaces and membranes generally, and through skin in particular. Importantly, the acyl lactylates of the present invention are able to enhance the permeability of drugs such that they can be delivered at therapeutically effective rates with reasonably sized transdermal delivery devices. Preferred acyl lactylate permeation enhancers of the present invention are caproyl lactylic acid and lauroyl lactylic acid.

Accordingly, the present invention provides a composition of matter for administration to a body surface or membrane to deliver at least one drug to the systemic circulation of a patient, at a therapeutically effective rate, by permeation through the body surface or membrane, comprising at least one drug and a permeation-enhancing amount of an acyl lactylate. The invention further provides a method for the transdermal coadministration of a drug at a therapeutically effective rate together with a skin permeation-enhancing amount of an acyl lactylate.

The system of the invention is preferably a transdermal drug delivery device comprising a matrix adapted to be placed in drug- and permeation enhancer-transmitting relation with the skin or mucosa. The system must be of a reasonable size useful for the application of the drug and the enhancer to a human body.

The invention is further directed to a composition of matter which optionally includes, in addition to the drug and acyl lactylate, one or more additional permeation enhancing compounds and to a method for the transdermal coadministration of such a composition.

DESCRIPTION OF THE INVENTION

Figure 1:
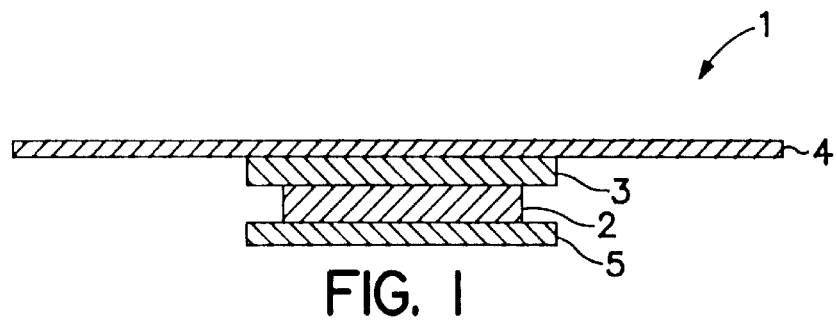
FIG. 1 is a cross-sectional view of one embodiment of a transdermal therapeutic drug delivery device which may be used in accordance with the present invention.

According to this invention, it has been discovered that acyl lactylates can be used to effectively enhance the permeability of drugs through body surfaces or membranes and particularly through the skin. Specifically, it has been found that acyl lactylates, when converted to a free acid form, enhance the permeability of the body surface or membrane to drugs or other biologically active agents such that therapeutically effective amounts of a drug or agent can be systemically delivered from reasonably sized devices at therapeutically effective rates. Additionally, it has been found that water dispersion of the acid form does not show corrosively low pH (pH 4.0–5.0).

It is believed that this invention has utility in connection with the delivery of drugs within the broad class normally delivered through body surfaces and membranes, including skin. In general, this includes therapeutic agents in all of the major areas, including, but not limited to, ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory agents, androgens, local and general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antithyroid agents, antitussives, antiviral agents, atypical antidepressants, azaspirodecanediones, barbituates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, 5-hydroxytryptamine antagonists, drugs for the treatment of hyperlipoproteinemia, hypnotics and sedatives, immunosupressive agents, laxatives, methylxanthines, monoamine oxidase inhibitors, neuromuscular blocking agents, organic nitrates, opiod analgesics and antagonists, pancreatic enzymes, phenothiazines, progestins, prostaglandins, agents for the treatment of psychiatric disorders, retinoids, sodium channel blockers, agents for spasticity and acute muscle spasms, succinimides, thioxanthines, thrombolytic agents, thyroid agents, tricyclic antidepressants, inhibitors of tubular transport of organic compounds, drugs affecting uterine motility, vasodilators, vitamins and the like.

Representative drugs include, by way of example and not for purposes of limitation, bepridil, diltiazem, felodipine, isradipine, nicardipine, nifedipine, nimodipine, nitredipine, verapamil, dobutamine, isoproterenol, carterolol, labetalol, levobunolol, nadolol, penbutolol, pindolol, propranolol, sotalol, timolol, acebutolol, atenolol, betaxolol, esmolol, metoprolol, albuterol, bitolterol, isoetharine, metaproterenol, pirbuterol, ritodrine, terbutaline, alclometasone, aldosterone, amcinonide, beclomethasone, dipropionate, betamethasone, clobetasol, clocortolone, cortisol, cortisone, corticosterone, desonide, desoximetasone, 11-desoxycorticosterone, 11-desoxycortisol, dexamethasone, diflorasone, fludrocortisone, flunisolide, fluocinolone, fluocinonide, fluorometholone, flurandrenolide, halcinonide, hydrocortisone, medrysone, 6α-methylprednisolone, mometasone, paramethasone, prednisolone, prednisone, tetrahydrocortisol, triamcinolone, benoxinate, benzocaine, bupivacaine, chloroprocaine, cocaine, dibucaine, dyclonine, etidocaine, lidocaine, mepivacaine, pramoxine, prilocaine, procaine, proparacaine, tetracaine, alfentanil, choroform, clonidine, cyclopropane, desflurane, diethyl ether, droperidol, enflurane, etomidate, fentanyl, halothane, isoflurane, ketamine hydrochloride, meperidine, methohexital, methoxyflurane, morphine, propofol, sevoflurane, sufentanil, thiamylal, thiopental, acetaminophen, allopurinol, apazone, aspirin, auranofin, aurothioglucose, colchicine, diclofenac, diflunisal, etodolac, fenoprofen, flurbiprofen, gold sodium thiomalate, ibuprofen, indomethacin, ketoprofen, meclofenamate, mefenamic acid, meselamine, methyl salicylate, nabumetone, naproxen, oxyphenbutazone, phenacetin, phenylbutazone, piroxicam, salicylamide, salicylate, salicylic acid, salsalate, sulfasalazine, sulindac, tolmetin, acetophenazine, chlorpromazine, fluphenazine, mesoridazine, perphenazine, thioridazine, trifluorperazine, triflupromazine, disopyramide, encainide, flecainide, indecainide, mexiletine, moricizine, phenytoin, procainamide, propafenone, quinidine, tocainide, cisapride, domperidone, dronabinol, haloperidol, metoclopramide, nabilone, prochlorperazine, promethazine, thiethylperazine, trimethobenzamide, buprenorphine, butorphanol, codeine, dezocine, diphenoxylate, drocode, hydrocodone, hydromorphone, levallorphan, levorphanol, loperamide, meptazinol, methadone, nalbuphine, nalmefene, nalorphine, naloxone, naltrexone, oxybutynin, oxycodone, oxymorphone, pentazocine, propoxyphene, isosorbide dinitrate, nitroglycerin, theophylline, phenylephrine, ephidrine, pilocarpine, furosemide, tetracycline, chlorpheniramine, ketorolac, bromocriptine, guanabenz, prazosin, doxazosin, and flufenamic acid.

Other representative drugs include benzodiazepines, such as alprazolam, brotizolam, chlordiazepoxide, clobazam, clonazepam, clorazepate, demoxepam, diazepam, flumazenil, flurazepam, halazepam, lorazepam, midazolam, nitrazepam, nordazepam, oxazepam, prazepam, quazepam, temazepam, triazolam, and the like; an antimuscarinic agent such as anisotropine, atropine, clidinium, cyclopentolate, dicyclomine, flavoxate, glycopyrrolate, hexocyclium, homatropine, ipratropium, isopropamide, mepenzolate, methantheline, oxyphencyclimine, pirenzepine, propantheline, scopolamine, telenzepine, tridihexethyl, tropicamide, and the like; an estrogen such as chlorotrianisene, siethylstilbestrol, methyl estradiol, estrone, estrone sodium sulfate, estropipate, mestranol, quinestrol, sodium equilin sulfate, 17β-estradiol (or estradiol), semi-synthetic estrogen derivatives such as the esters of natural estrogen, such as estradiol-17β-enanthate, estradiol-17β-valerate, estradiol-3-benzoate, estradiol-17β-undecenoate, estradiol 16,17-hemisuccinate or estradiol-17β-cypionate, and the 17-alkylated estrogens, such as ethinyl estradiol, ethinyl estradiol-3-isopropylsulphonate, and the like; an androgen such as danazol, fluoxymesterone, methandrostenolone, methyltestosterone, nandrolone decanoate, nandrolone phenpropionate, oxandrolone, oxymetholone, stanozolol, testolactone, testosterone, testosterone cypionate, testosterone enanthate, testosterone propionate, and the like; or a progestin such as ethynodiol diacetate, gestodene, hydroxyprogesterone caproate, levonorgestrel, medroxyprogesterone acetate, megestrol acetate, norethindrone, norethindrone acetate, norethynodrel, norgestrel, progesterone, and the like.

Administration of the drug according to the invention comprises administering the drug at a therapeutically effective rate to an area of a body surface or membrane and simultaneously administering an acyl lactylate to the area of the body surface or membrane at a rate sufficient to substantially increase the permeability of the area to the drug formulation.

According to the invention, an acyl lactylate permeation enhancer and the drug to be delivered are placed in drug- and acyl lactylate-transmitting relationship to the appropriate body surface, preferably in a carrier therefore, and maintained in place for the desired period of time. The drug and acyl lactylate are typically dispersed within a physicochemically and biologically compatible matrix or carrier which may be applied directly to the body surface or skin as an ointment, gel, cream, suppository or sublingual or buccal tablet, for example, but are more preferably administered from a transdermal therapeutic delivery device as more fully described below. When used in the form of a liquid, ointment, cream, or gel applied directly to the skin, it is preferable, although not required, to occlude the site of administration. Such compositions can also contain other permeation enhancers, stabilizers, dyes, diluents, pigments, vehicles, inert fillers, excipients, gelling agents, vasoconstrictors, and other components of typical compositions as are known to the art.

The acyl lactylates of this invention have a permeation-enhancing effect on the transport of drugs through body surface tissues generally, in addition to the skin. However, because skin is one of the most effective body barriers to the permeation of foreign substances, the effect of acyl lactylates on skin permeation makes it extremely useful in transdermal delivery. The following description of embodiments of the invention is therefore directed primarily to improving systemic delivery of these drugs by permeation through the skin.

It may be desirable in certain instances or with certain drugs to include one or more additional permeation enhancers in combination with the acyl lactylate. Thus, in certain embodiments of the present invention, a second permeation enhancer is included together with the drug and acyl lactylate permeation enhancer. This second enhancer may be selected from those compounds that have a permeation-enhancing effect with the drug and are compatible with the drug and with the acyl lactylate. For example, the second permeation enhancer may be a monoglyceride or mixture of monoglycerides of fatty acids such as glycerol monolaurate (GML) or glycerol monooleate (GMO), lauramide diethanolamine (LDEA), esters of fatty acids having from about 10 to 20 carbon atoms, and/or a lower $C_{1-4}$ alcohol such as ethanol or isopropanol.

Typically, monoglycerides have been available as a mixture of monoglycerides of fatty acids with one monoglyceride being the principal component, from which component the mixture derives its name. For example, one commercial monoglyceride is Emerest 2421 glycerol monooleate (Emery Division, Quantum Chemical Corp.), which is a mixture of glycerol oleates with a glycerol monooleate content of 58% and a total monoesters content of 58%. Other examples of commercial monoglycerides are Myverol 1899K glycerol monooleate (Eastman Chemical Products) which has a glycerol monooleate content of 61% and a total monoesters content of 93%, and Myverol 1892K glycerol monolinoleate which has a glycerol monolinoleate content of 68% and a minimum total monoesters content of 90%. The monoesters are chosen from those with from 10 to 20 carbon atoms. The fatty acids may be saturated or unsaturated and include, for example, lauric acid, myristic acid, stearic acid, oleic acid, linoleic acid and palmitic acid. Monoglyceride permeation enhancers include glycerol monooleate, glycerol monolaurate and glycerol monolinoleate, for example. In a presently preferred embodiment of this invention, the second permeation enhancer is a monoglyceride or a mixture of monoglycerides of unsaturated fatty acids, and more preferred is glycerol monolaurate (GML). As used herein and in the appended claims, the term "monoglyceride" refers to a monoglyceride or a mixture of monoglycerides of fatty acids.

It has been seen that glycerol monooleate having a total monoesters content of less than about 65% interacts adversely with known adhesive materials to such an extent that the adhesive cannot function to maintain a delivery device on the skin. Therefore, when an in-line adhesive is present as a part of the device of the invention so that a permeation enhancer must pass through the adhesive, and when glycerol monooleate is utilized as the second permeation enhancer, the glycerol monooleate must have a total monoesters content of at least 65%.

The permeation-enhancing mixture is dispersed throughout the matrix or carrier, preferably at a concentration sufficient to provide permeation-enhancing amounts of enhancer in the reservoir throughout the anticipated administration period. Where there is an additional, separate permeation enhancer matrix layer as well, as in FIG. 2, the permeation enhancer normally is present in the separate reservoir in excess of saturation.

Figure 3:
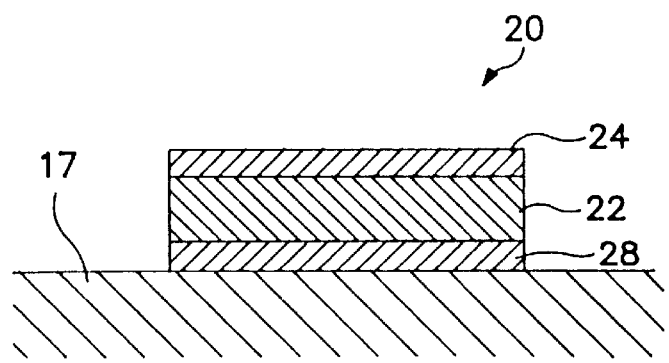
FIG. 3 is a cross-sectional view of yet another embodiment of a transdermal therapeutic drug delivery device which may be used in accordance with this invention.

One embodiment of a transdermal delivery device of the present invention is illustrated in FIG. 1. In FIG. 1, device 1 is comprised of a drug- and acyl lactylate-containing reservoir ("drug reservoir") 2 which is preferably in the form of a matrix containing the drug and the enhancer dispersed therein. In those embodiments which include a mixture of permeation enhancers, drug reservoir 2 also includes these additional enhancers. A backing layer 3 is provided adjacent one surface of drug reservoir 2. Adhesive overlay 4 maintains the device 1 on the skin and may be fabricated together with, or provided separately from, the remaining elements of the device. With certain formulations, the adhesive overlay 4 may be preferable to an in-line contact adhesive, such as adhesive layer 28 as shown in FIG. 3. Backing layer 3 is preferably slightly larger than drug reservoir 2, and in this manner prevents the materials in drug reservoir 2 from adversely interacting with the adhesive in overlay 4. A strippable or removable liner 5 is also provided with device 1 and is removed just prior to application of device 1 to the skin.

Figure 2:
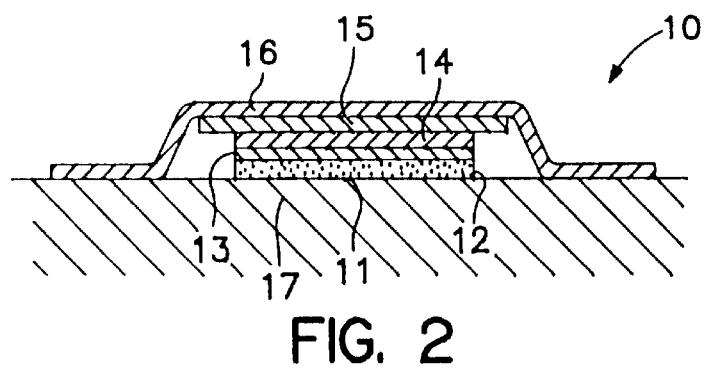
FIG. 2 is a cross-sectional view of another embodiment of a transdermal therapeutic drug delivery device which may be used in accordance with the present invention.

FIG. 2 illustrates another embodiment of the invention, device 10, shown in placement on the skin 17. In this embodiment, the transdermal delivery device 10 comprises a multi-laminate drug formulation/enhancer reservoir 11 having at least two zones 12 and 14. Zone 12 consists of a drug reservoir substantially as described with respect to FIG. 1. Zone 14 comprises a permeation enhancer reservoir which is preferably made from substantially the same matrix as is used to form zone 12. Zone 14 comprises an acyl lactylate dispersed throughout, preferably in excess of saturation, and is substantially free of any undissolved drug. One or more additional permeation enhancers may optionally be included in zone 14 as well. A rate-controlling membrane 13 for controlling the release rate of the acyl lactylate and, optionally, any additional enhancers from zone 14 to zone 12 is placed between the two zones. A rate-controlling membrane (not shown) for controlling the release rate of the enhancer from zone 12 to the skin may also optionally be utilized and would be present between the skin 17 and zone 12.

The rate-controlling membrane may be fabricated from permeable, semipermeable or microporous materials which are known in the art to control the rate of agents into and out of delivery devices and having a permeability to the permeation enhancer lower than that of zone 12. Suitable materials include, but are not limited to, polyethylene, polyvinyl acetate and ethylene vinyl acetate copolymers.

An advantage of the device described in FIG. 2 is that the drug-loaded zone 12 is concentrated at the skin surface rather than throughout the entire mass of the reservoir 11. This functions to reduce the amount of drug in the device while maintaining an adequate supply of the permeation enhancer or mixture.

Superimposed over the drug formulation/enhancer-reservoir 11 of device 10 is a backing 15 and an adhesive overlay 16 as described above with respect to FIG. 1. In addition, a strippable liner (not shown) would preferably be provided on the device prior to use as described with respect to FIG. 1 and removed prior to application of the device 10 to the skin 17.

In the embodiments of FIGS. 1 and 2, the carrier or matrix material has sufficient viscosity to maintain its shape without oozing or flowing. If, however, the matrix or carrier is a low viscosity flowable material, the composition can be fully enclosed in a dense non-porous or microporous skin-contacting membrane, as known to the art from U.S. Pat. No. 4,379,454 (noted above), for example.

An example of a presently preferred transdermal delivery device is illustrated in FIG. 3. In FIG. 3, transdermal delivery device 20 comprises a drug reservoir 22 containing together the drug and the acyl lactylate permeation enhancer. Optionally, one or more additional permeation enhancers may also be included in drug reservoir 22. Reservoir 22 is preferably in the form of a matrix containing the drug and the enhancer dispersed therein. Reservoir 22 is sandwiched between a backing layer 24, which is impermeable to both the drug and the acyl lactylate, and an in-line contact adhesive layer 28. In FIG. 3, the drug reservoir 22 is formed of a material, such as a rubbery polymer, that is sufficiently viscous to maintain its shape. The device 20 adheres to the surface of the skin 17 by means of the contact adhesive layer 28. The adhesive for layer 28 should be chosen so that it is compatible and does not interact with any of the drug or, in particular, the acyl lactylate permeation enhancer. The adhesive layer 28 may optionally contain permeation enhancer and/or drug. A strippable liner (not shown) is normally provided along the exposed surface of adhesive layer 28 and is removed prior to application of device 20 to the skin 17. In an alternative embodiment, a rate-controlling membrane (not shown) is present and the drug reservoir 22 is sandwiched between backing layer 24 and the rate-controlling membrane, with adhesive layer 28 present on the skin-side of the rate-controlling membrane.

Various materials suited for the fabrication of the various layers of the transdermal devices of FIGS. 1, 2 or 3 are known in the art or are disclosed in the aforementioned transdermal device patents previously incorporated herein by reference.

The matrix making up the drug/acyl lactylate permeation enhancer reservoir can be a gel or a polymer. Suitable materials should be compatible with the drug and enhancer and any other components in the system. The matrix may be aqueous or non-aqueous based. Aqueous formulations typically comprise water or water/ethanol and about 1–5 wt % of a gelling agent, an example being a hydrophilic polymer such as hydroxyethylcellulose or hydroxypropylcellulose. Typical non-aqueous gels are comprised of silicone fluid or mineral oil. Mineral oil based gels also typically contain 1–2 wt % of a gelling agent such as colloidal silicon dioxide. The suitability of a particular gel depends upon the compatibility of its constituents with the drug and the permeation-enhancing mixture in addition to any other components in the formulation.

When using a non-aqueous based formulation, the reservoir matrix is preferably composed of a hydrophobic polymer. Suitable polymeric matrices are well known in the transdermal drug delivery art, and examples are listed in the above-named patents previously incorporated herein by reference. A typical laminated system would consist essentially of a polymeric membrane and/or matrix such as ethylene vinyl acetate (EVA) copolymers, such as those described in U.S. Pat. No. 4,144,317, prefeably having a vinyl acetate content in the range of from about 9% to about 60% and more preferably about 9% to 40% vinyl acetate. Polyisobutylene/oil polymers containing from 4–25% high molecular weight polyisobutylene and 20–81% low molecular weight polyisobutylene with the balance being an oil such as mineral oil or polyisobutynes may also be used as the matrix material.

In addition to a drug and acyl lactylate, which are essential to the invention, the matrix may also contain stabilizers, dyes, pigments, inert fillers, tackifiers, excipients and other conventional components of transdermal delivery devices as are known in the art.

The amounts of the drug that are present in the therapeutic device, and that are required to achieve a therapeutic effect, depend on many factors, such as the minimum necessary dosage of the particular drug; the permeability of the matrix, of the adhesive layer and of the rate-controlling membrane, if present; and the period of time for which the device will be fixed to the skin. There is, in fact, no upper limit to the maximum amounts of drug present in the device. The minimum amount of each drug is determined by the requirement that sufficient quantities of drug must be present in the device to maintain the desired rate of release over the given period of application.

The drug is generally dispersed through the matrix at a concentration in excess of saturation, i.e. at unit activity. The amount of excess is determined by the intended useful life of the system. However, the drug may be present at initial levels below saturation without departing from this invention. Generally, the drug may be present at initially subsaturated levels when: 1) the skin flux of the drug is sufficiently low such that the reservoir drug depletion is slow and small; 2) non-constant delivery of the drug is desired or acceptable; and/or 3) saturation of the reservoir is achieved in use due to migration of water into the reservoir from the skin, where water is abundantly available.

The acyl lactylate permeation enhancer is dispersed throughout the matrix, preferably at a concentration sufficient to provide permeation-enhancing concentrations of enhancer in the reservoir throughout the anticipated administration period.

In certain embodiments of the invention, one or more additional permeation enhancers, such as a monoglyceride or mixture of monoglycerides of fatty acids including glycerol monolaurate (GML) and glycerol monooleate (GMO), lauramide diethanolamine (LDEA), esters of fatty acids having from about 10 to 20 carbon atoms, and/or a lower $C_{1-4}$ alcohol such as ethanol or isopropanol, may also be dispersed throughout the matrix, preferably at a concentration sufficient to provide permeation-enhancing concentrations of enhancer in the drug reservoir throughout the anticipated administration period.

In the present invention, the drug is delivered through the skin or other body surface at a therapeutically effective rate (that is, a rate that provides an effective therapeutic result) and the acyl lactylate permeation enhancer is delivered at a permeation-enhancing rate (that is, a rate that provides increased permeability of the application site to the drug) for a predetermined time period.

A preferred embodiment of the present invention is a monolith such as that illustrated in FIG. 3 (either with or without a rate-controlling membrane) wherein reservoir 22 comprises, by weight, 30–90% polymer (preferably EVA with a vinyl acetate content of 40%), 0.01–40% drug, and 1–70% of an acyl lactylate. The in-line adhesive layer 28 contains an adhesive which is compatible with the permeation enhancer. In another preferred embodiment of the invention, a monolith such as that in FIG. 3 includes reservoir 22 comprising, by weight, 30–90% polymer (preferably EVA with a vinyl acetate content of 40%), 0.01–40% drug, 1–70% acyl lactylate, and 1–45% of a second permeation enhancer, preferably GML.

The devices of this invention can be designed to effectively deliver a drug for an extended time period of up to 7 days or longer. Seven days is generally the maximum time limit for application of a single device because the skin site may be affected by a period of occlusion greater than 7 days, or other problems such as the system or edges of the system lifting off of the skin may be encountered over such long periods of application. Where it is desired to have drug delivery for greater than 7 days (such as, for example, when a hormone is being applied for a contraceptive effect), when one device has been in place on the skin for its effective time period, it is replaced with a fresh device, preferably on a different skin site.

The transdermal therapeutic devices of the present invention are prepared in a manner known in the art, such as by those procedures, for example, described in the transdermal device patents listed previously herein. The following examples are offered to illustrate the practice of the present invention and are not intended to limit the invention in any manner.

EXAMPLE 1

Figure 4:
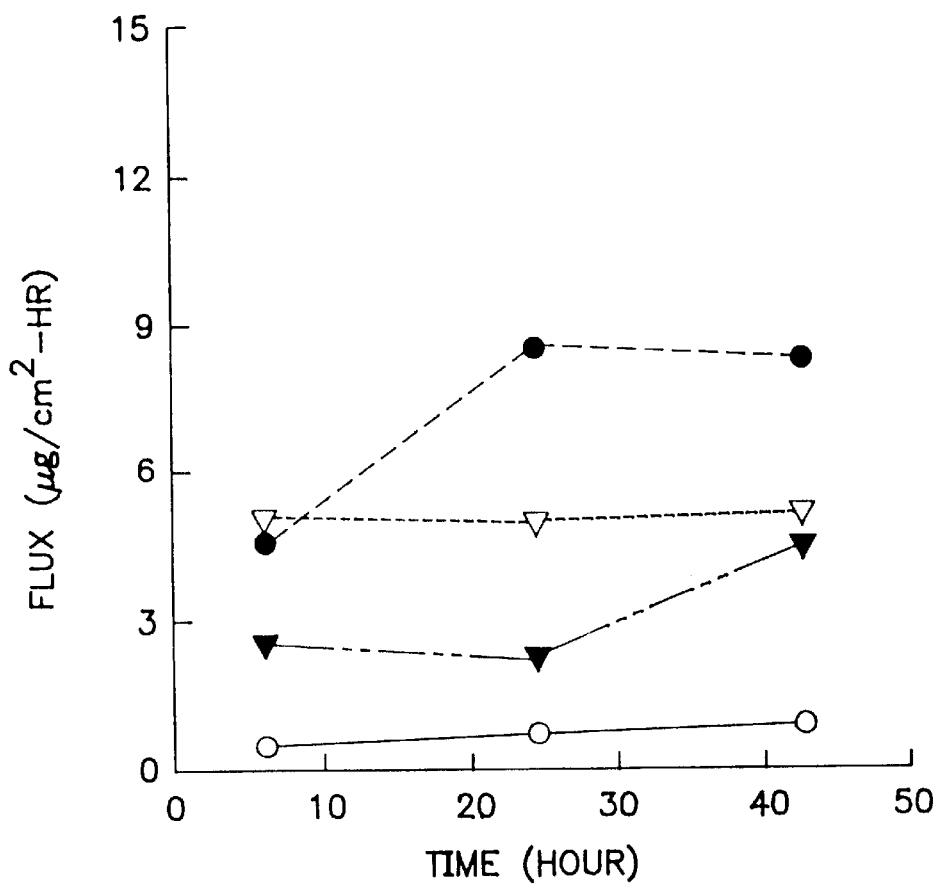
FIG. 4 is a graph of the flux of progesterone through human epidermis at 35° C., in vitro, from a mineral oil system with various permeation enhancers.

Several test samples were made to measure the progesterone flux through human cadaver skin from donor vehicles containing progesterone at saturation in mineral oil. The progesterone vehicle was also mixed with 20% by weight caproyl lactylic acid or lauroyl lactylic acid, or dispersed with 1.1% by weight glycerol monolaurate. Transdermal fluxes were obtained using human epidermis at 35° C. in standard diffusion cells. As seen in FIG. 4, the progesterone mixtures with caproyl lactylic acid and lauroyl lactylic acid demonstrated superior flux of progesterone through skin.

EXAMPLE 2

Figure 5:
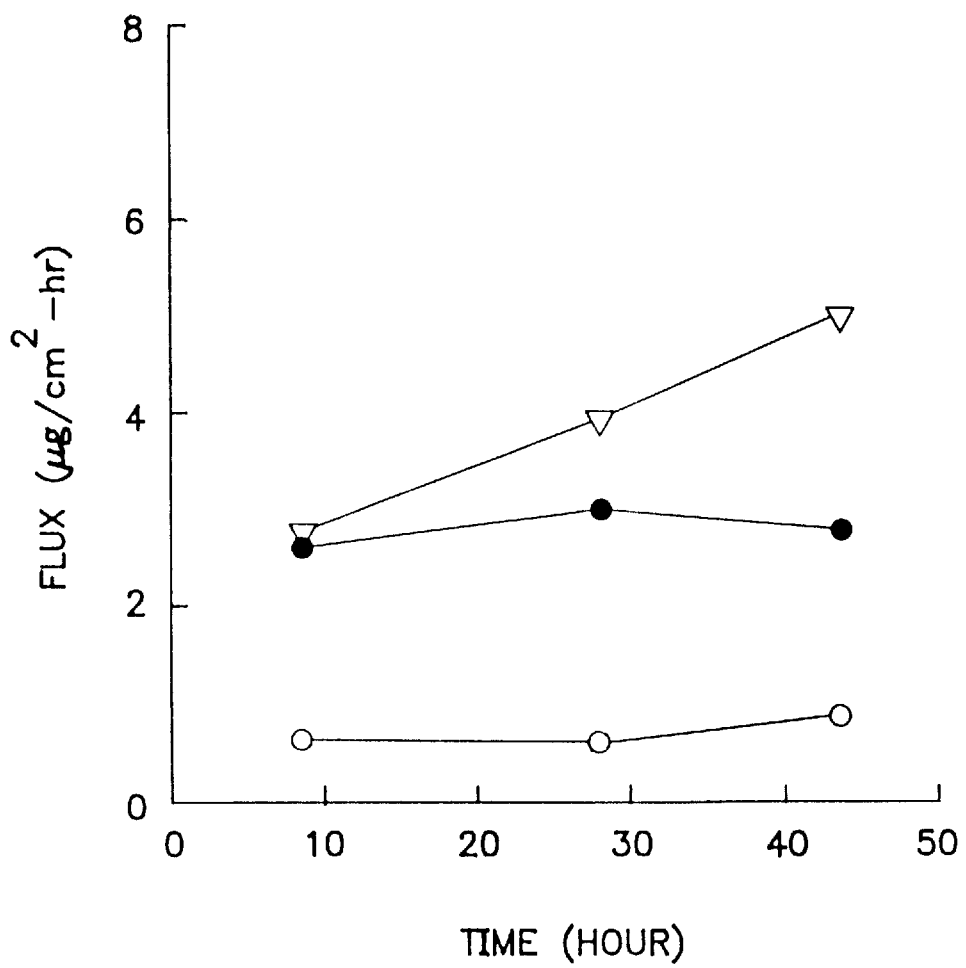
FIG. 5 is a graph of the flux of testosterone through human epidermis at 35° C., in vitro, from a mineral oil system with various permeation enhancers.

Several test samples were made to measure the testosterone flux through human cadaver skin. Testosterone saturated in mineral oil was used as a control, and was compared with mixtures including 12% GML/7% caproyl lactylic acid, or 12% GML/7% lauroyl lactylic acid. Transdermal fluxes were obtained using human epidermis at 35° C. in standard diffusion cells. As demonstrated in FIG. 5, the solutions containing the GML/acyl lactylate mixtures resulted in a testosterone flux through skin at least double that of the control.

EXAMPLE 3

The drug/permeation enhancer reservoirs were prepared by mixing ethylene vinyl acetate having a vinyl acetate content of 40 percent ("EVA 40", USI Chemicals, Illinois) in an internal mixer (Brabender type mixer) until the EVA 40 pellets fused. Testosterone, lauroyl lactylic acid (LLA), caproyl lactylic acid (CLA), GML, lactic acid (LA), M-DEA, L-DEA, or lauryl lactate (LL) were then added as shown in Table 1. The mixture was blended, cooled and calendered to a 5 mil thick film.

The film was then laminated to a Medpar® (3M) backing on one side and an acrylate contact adhesive (3M) on the opposite side. The laminate was then cut into 1.98 cm² circles using a steel punch.

Circular pieces of human epidermis were mounted on horizontal permeation cells with the stratum corneum facing the donor compartment of the cell. The release liner of the laminate was removed and the systems were centered over the stratum corneum side of the epidermis. The cells were then masked. A known volume of receptor solution (20 ml) was equilibrated at 35° C. and placed in the receptor compartment. Air bubbles were removed from the receptor compartment, the cell was capped and placed in a water bath shaker at 35° C.

TABLE 1

Drug/Permeation Enhancer Reservoir (wt %)

| RESERVOIR FORMULATION | WEIGHT PERCENT |
|---|---|
| Testosterone/LLA/GML/EVA 40 | 10/20/20/50 |
| Testosterone/CLA/L-DEA/EVA 40 | 10/20/20/50 |
| Testosterone/LL/LA/GML/EVA 40 | 10/12/3/20/55 |
| Testosterone/LL/LA/L-DEA/EVA 40 | 10/12/3/20/55 |
| Testosterone/LLA/M-DEA/EVA 40 | 10/20/20/50 |
| Testosterone/LL/LA/M-DEA/EVA 40 | 10/12/3/20/55 |
| Testosterone/EVA 40 | 2/98 |

Figure 6A:
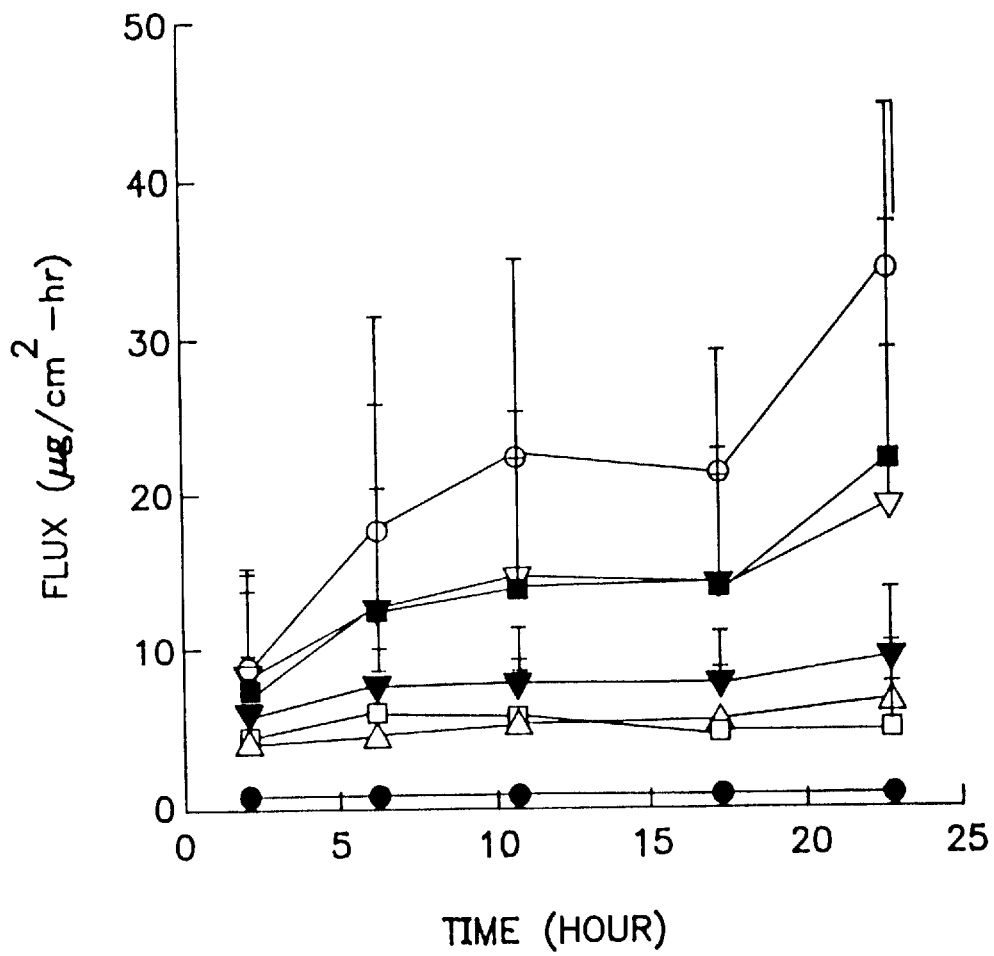
FIG. 6 is a graph of the flux of testosterone through human epidermis at 35° C., in vitro, from an EVA matrix system with various permeation enhancers.

At given time intervals, the entire receptor solution was removed from the cells and replaced with an equal volume of fresh receptor solutions previously equilibrated at 35° C. The receptor solutions are stored in capped vials at room temperature until assayed for testosterone content by HPLC. From the drug concentration and the volume of the receptor solutions, the area of permeation and the time interval, the flux of the drug through the epidermis was calculated as follows: (drug concentration×volume of receptor)/(area× time)=flux ($\mu$g/cm²·hr). The flux of the testosterone achieved from the various systems is shown in FIG. 6. As demonstrated in FIG. 6, formulations comprising mixtures including lauroyl lactylic acid or caproyl lactylic acid resulted in superior flux of testosterone through the skin.

This invention has been described in detail with particular reference to certain preferred embodiments thereof, but it will be understood that variations and modifications can be effected within the spirit and scope of the invention.

What is claimed is:

1. A method for enhancing the transdermal flux during transdermal administration of at least one drug to the systemic circulation of a patient, at a therapeutically effective rate, by permeation through a body surface or membrane, comprising:
    (a) simultaneously administering, to the body surface or membrane, at least one drug; and
    (b) a permeation-enhancing amount of an acyl lactylate permeation enhancer represented by the general structure R—CO—(OCHCH$_3$CO)$_n$—OH where R is a straight or branched alkyl or aryl group consisting of 3 to 20 carbons and n=1 to 10; sufficient to substantially increase the permeability of the body surface or membrane to the drug in order to systemically deliver said drug to a patient at a therapeutically effect rate.

2. A method according to claim 1 further comprising simultaneously coadministering a permeation-enhancing amount of one or more of the permeation enhancers selected from the group consisting of monoglycerides or mixtures of monoglycerides of fatty acids, lauramide diethanolamine, esters of fatty acids having from about 10 to 20 carbon atoms, and lower C$_{1-4}$ alcohols.

3. A method according to claim 1 wherein the acyl lactylate is lauroyl lactylic acid.

4. A method according to claim 1 wherein the acyl lactylate is caproyl lactylic acid.

5. A method according to claim 1 wherein the drug is testosterone.

6. A method according to claim 1 wherein the drug is progesterone.

7. A method according to claim 1 wherein the drug is administered to the systemic circulation of said patient at a therapeutically effective rate throughout a substantial portion of an administration period of at least about 10 hours.

8. A method for enhancing the flux of a drug administered from a transdermal drug delivery device through a body surface or membrane, said device of the type comprising a backing layer, a drug reservoir layer on the skin proximal side of the backing layer and a means for maintaining the device in drug transmitting relationship with said body surface or membrane throughout an administration period, said method comprising:
    providing said transdermal drug delivery device with an acyl lactylate permeation enhancer in an amount sufficient to substantially increase the permeability of the body surface or membrane to the drug in order to systemically deliver said drug to a patient at a therapeutically effective rate, said acyl lactylate being represented by the general structure R—CO—(OCHCH$_3$CO)$_n$—OH where R is a straight or branched alkyl or aryl group consisting of 3 to 20 carbon atoms and n=1 to 10.

9. The method according to claim 8 wherein the acyl lactylate is selected from lauroyl lactylic acid and caproyl lactylic acid.

10. The method according to claim 8 wherein the drug is selected from testosterone and progesterone.

11. The method according to claim 8 wherein the acyl lactylate is dispersed within the drug reservoir.

12. The method of claim 11 wherein the means for maintaining the device in drug transmitting relationship comprises a separate adhesive layer.

13. The method according to claim 8 wherein the means for maintaining the device in drug transmitting relationship comprises a pressure sensitive adhesive which also functions as the drug reservoir.

14. A device for the trandermal administration of at least one drug to the systemic circulation of a patient at a therapeutically effective rate, by permeation through a body surface or membrane, comprising:
    (a) a first reservoir comprising at least one drug and a permeation enhancing-amount of an acyl lactylate permeation enhancer represented by the general structure R—CO—(OCHCH$_3$CO)$_n$—OH where R is a straight or branched alkyl or aryl group consisting of 3 to 20 carbons and n=1 to 10;
    (b) a second reservoir comprising an additional amount of said permeation enhancer and substantially free of said drug;

(c) a rate controlling membrane between the first reservoir and the second reservoir, said first reservoir positioned on the skin facing side of said rate controlling membrane and said second reservoir positioned on the skin-distal side of said rate controlling membrane;

(d) means for maintaining said first and second reservoirs in drug- and permeation enhancer- transmitting relation with the body surface or membrane, wherein the drug is delivered to the systemic circulation of a patient at a therapeutically effective rate.

15. A device according to claim 14 wherein the acyl lactylate is caproyl lactylic acid.

16. A device according to claim 14 wherein the acyl lactylate is lauroyl lactylic acid.

17. A device according to claim 14 wherein the drug is testosterone.

18. A device according to claim 14 wherein the drug is progesterone.

19. A device according to claim 14 wherein the acyl lactylate permeation enhancer is combined with a permeation-enhancing amount of one or more of the permeation enhancers selected from the group consisting of monoglycerides or mixtures of monoglycerides of fatty acids, lauramide diethanolamine, esters of fatty acids having from about 10 to 20 carbon atoms, and lower $C_{1-4}$ alcohols.

* * * * *